(12) United States Patent
Galloni

(10) Patent No.: US 9,877,690 B2
(45) Date of Patent: Jan. 30, 2018

(54) C-ARM OF MEDICAL IMAGING SYSTEM

(71) Applicant: GENERAL ELECTRIC COMPANY, Schenectady, NY (US)

(72) Inventor: Bruno Galloni, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 227 days.

(21) Appl. No.: 14/761,728

(22) PCT Filed: Jan. 17, 2013

(86) PCT No.: PCT/IB2013/000159
§ 371 (c)(1),
(2) Date: Jul. 17, 2015

(87) PCT Pub. No.: WO2014/111741
PCT Pub. Date: Jul. 24, 2014

(65) Prior Publication Data
US 2016/0000391 A1   Jan. 7, 2016

(51) Int. Cl.
A61B 6/00 (2006.01)
(52) U.S. Cl.
CPC .......... A61B 6/4441 (2013.01); A61B 6/4452 (2013.01)
(58) Field of Classification Search
CPC .. A61B 6/00; A61B 6/035; A61B 6/44; A61B 6/4429; A61B 6/4435; A61B 6/4441; A61B 6/4452; A61B 6/588; A61B 6/589

USPC .................................. 378/11, 13, 189, 204
See application file for complete search history.

(56) References Cited

U.S. PATENT DOCUMENTS

| 4,358,856 A | 11/1982 | Stivender et al. |
| 6,325,537 B1 | 12/2001 | Watanabe |
| 2008/0198973 A1 | 8/2008 | Timmermans et al. |
| 2009/0180594 A1 | 7/2009 | Saladin et al. |
| 2010/0303207 A1 | 12/2010 | Tsujii et al. |

FOREIGN PATENT DOCUMENTS

| CN | 201227280 Y | 4/2009 |
| JP | 2004357987 A | 12/2004 |
| WO | 2007026282 A2 | 3/2007 |

OTHER PUBLICATIONS

Japanese Search Report issued in connection with corresponding JP Application No. 2015-553173 dated Dec. 12, 2016.
CN Office Action issued in connection with corresponding CN Application No. CN201380070837.7 dated Apr. 5, 2017.

Primary Examiner — Jurie Yun

(57) ABSTRACT

A C-arm of a medical imaging system, comprising a C-shaped structure, a radiation detector support and a connection linking said support to said C-shaped structure so that said support can move toward and away from an end of said C-shaped structure, wherein said connection is structured so as to be bendable to reduce its bulk.

18 Claims, 1 Drawing Sheet

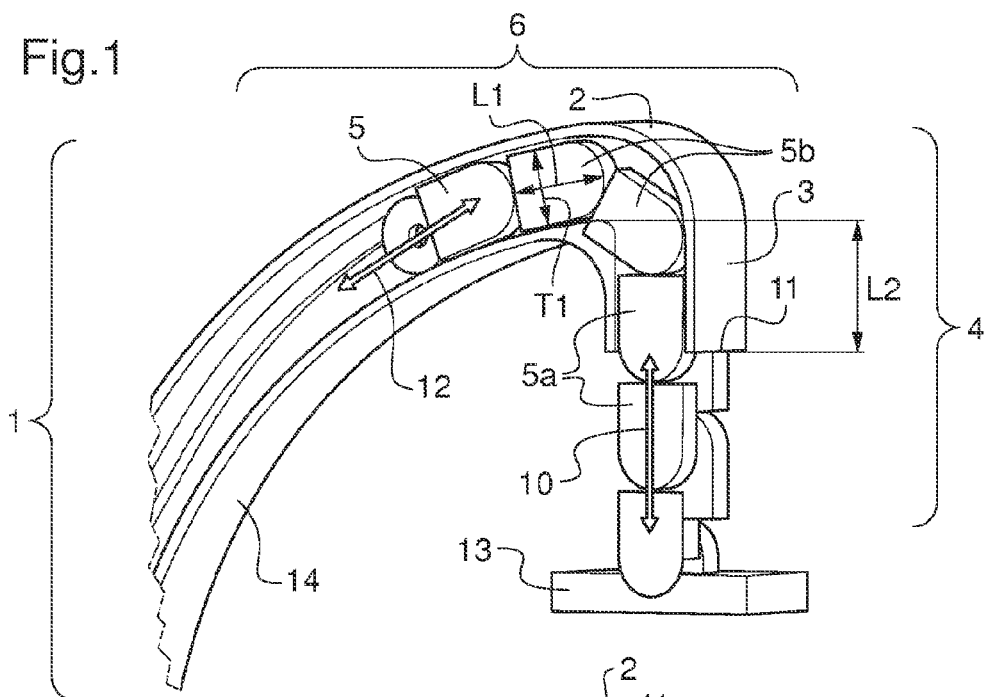
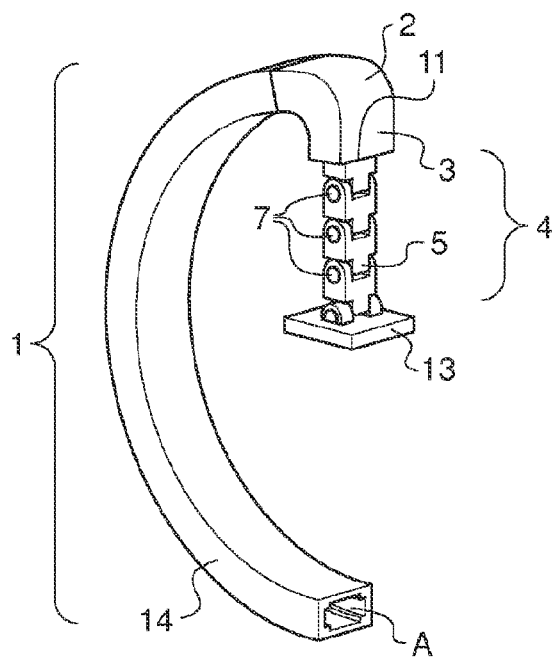
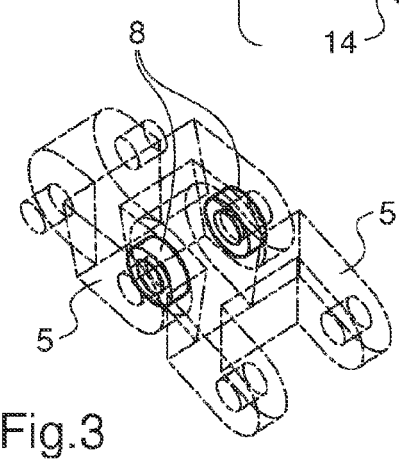
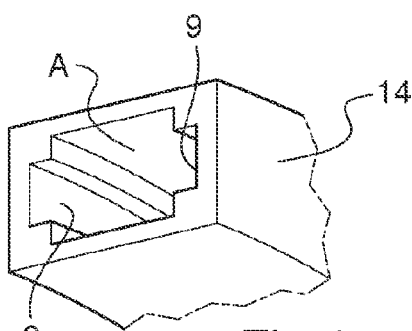

C-ARM OF MEDICAL IMAGING SYSTEM

FIELD OF THE INVENTION

Embodiments of the present invention relate to a C-arm of a medical imaging system. More particularly, embodiments of the present invention relate to a connection linking a radiation detector support to a C-shaped structure so that the radiation detector support can move toward and away from an end of the C-shaped structure.

BACKGROUND OF THE INVENTION

According to a prior art, it is known a rigid, fixed and straight, connection linking radiation detector support to C-shaped structure which moves like a lift. So, this connection and the radiation detector support and the radiation detector, all fixed and integral with one another, move simultaneously upwards and downwards in a rectilinear motion. In this prior art, when the object image distance (OID) in the C-arm is set to maximum, the connection projects, outwards the C-shaped structure, far away beyond the end of the C-shaped structure. This presents the drawback that, when the C-arm rotates, it will run the risk to interfere with the floor of the room where the medical imaging system stands. Therefore, when using this prior art, in the configuration where the C-arm rotates, the highest values of object image distance cannot be used. So this prior art presents the drawback that the object image distance is limited because of the presence of the lift, in the configurations where the C-arm rotates.

SUMMARY OF THE INVENTION

The object of embodiments of the present invention is to alleviate at least partly the above mentioned drawbacks.

More particularly, an embodiment provides a C-arm which connection between radiation detector support and C-shaped structure presents a limited bulk in all configurations, even when the C-arm rotates. This connection is structured so that it can be bent so that its bulk is reduced as compared to the situation where it is not bent. Reducing bulk means not necessarily reducing the global volume but at least reducing one dimension of the connection, and more particularly reducing a dimension of the connection so that the connection projection beyond the end of the C-shaped structure is reduced compared to the connection projection beyond the end of the C-shaped structure if such dimension had not been reduced.

This object, according to an embodiment, is achieved with a C-arm of a medical imaging system, comprising a C-shaped structure, a radiation detector support and a connection linking said support to said C-shaped structure so that said support can move toward and away from an end of said C-shaped structure, wherein said connection is structured so as to be bendable to reduce its bulk. Said connection can be bent in such a way that its bulk is reduced. For example, when said connection is bent, the biggest dimension of the connection is reduced.

Another object of embodiments of the present invention can be achieved with a system comprising a structure, a mobile element and a connection linking said mobile element to said structure so that said mobile element can move toward and away from said structure, wherein said connection is bendable to reduce its bulk. This another object of the invention can deal with systems outside the field of C-arm of medical imaging system. In an embodiment, part of said connection is guided and part of said connection is not guided, at least for one position of said mobile element, more particularly for most of positions of said mobile element. More particularly, said connection is bendable to become storable inside said structure.

More particularly, embodiments comprise one or more of the following features, which can be taken separately or together, either in partial combination or in full combination.

In an embodiment, said connection is disposed so as not to project, outwards said C-shaped structure, beyond said end of said C-shaped structure. Therefore, not only some highest object image distances can be used, but also the maximal object image distance can be used too, without any notable risk of interference between the C-arm and the floor, when the C-arm rotates. The bulk of the connection outwards the C-arm is then much reduced.

In an embodiment, said connection is partly stored in a casing when said support is farthest from said end of said C-shaped structure, wherein the whole part of said connection which is outside said casing is rigidly straight, and wherein at least part of said connection which is inside said casing is bent. This allows for optimizing the compromise between the image stability and the connection bulk.

In an embodiment, the whole part of said connection which comes out of said casing is automatically locked in straight position before it comes out of said casing and part of said connection which comes into said casing is automatically made bendable after it comes into said casing. That way, the locking in straight position is only performed when useful, that is to say outside the casing, and as soon as this locking in straight position is no more needed, it is unlocked again and becomes bendable.

In an embodiment, said C-shaped structure is at least partly hollow and said connection can be at least partly, or in an embodiment completely, stored in said hollow C-shaped structure when said support is closest to said end of said C-shaped structure. That way, the bulk of the connection when stored is minimized, because no additional free space is then needed for the storage of the connection.

In an embodiment, an area of a hollow section of said C-shaped structure is at least more than a half an area of a total section of said C-shaped structure. A notable part of the interior of the C-shaped structure is used as a storage room for the connection when needed, instead of being useless and wasted space.

In an embodiment, said hollow C-shaped structure successively comprises, from said end of said hollow C-shaped structure, a hollow straight portion and a hollow bent portion, through which both portions said connection can move forward and backward. The hollow bent portion allows redirect the connection from outside the C-shaped structure to storage room or vice-versa. The hollow straight portion allows align the different portions of the connection before coming out of the C-shaped structure.

In an embodiment, said connection comprises a chain including several links rotary articulated together. This is a simple and efficient realization mode of this bendable connection, which makes then quite easy to achieve the compromise between flexibility of connection when stored and rigid linearity of connection when outside of C-shaped structure.

In an embodiment, said hollow straight portion presents a length which ranges from 1.1 to 1.5 the length of an articulated link. This allows simultaneously minimizing the bulk of the extension of the C-shaped structure while keeping a length of this extension which is sufficient to align properly the links of the chain before they come out of their storage room located inside the C-shaped structure.

In an embodiment, said connection comprises an actuator adapted to push said chain to spread it and to pull said chain to store it. That way, manipulation of the chain is made simpler.

In an embodiment, said chain includes between 4 and 12 articulated links. In an embodiment, said chain includes between 6 and 10 articulated links. For example, said chain includes between 7 or 8 articulated links. This allows for a good compromise between the needed flexibility or bendability of the chain when stored and a relative simplicity of the chain to get the needed rigid linearity of the chain when outside the C-shaped structure.

More particularly, the embodiments described above may also comprise one or more of the following features, which can be taken separately or together, either in partial combination or in full combination, which deal with precise shaping of the links of the chain allowing for a more efficient and useful connection.

In an embodiment, said articulated links having a length in direction of their displacement and a thickness in direction of a curvature of said C-shaped structure, said length is bigger than said thickness, said length in an embodiment ranges from 1.1 to 2 times said thickness, and said length more particularly ranges from 1.3 to 1.7 times said thickness.

In an embodiment, said articulated links having a length in direction of their displacement, said length ranges from 80 mm to 150 mm, more particularly ranges from 100 mm to 130 mm.

In an embodiment, said articulated links present a convex shape at the front, and in an embodiment also present a flat shape at the rear, front of said articulated links being stored before rear of said articulated links. In another option, said articulated links present a convex shape at the front, and wherein said articulated links more particularly present a flat shape at the rear, front of said articulated links being spread before rear of said articulated links. This correspondence of a convex shape of a link with the flat shape of the neighboring link allows for a more fluid articulation between two adjacent links when the chain is bent.

In an embodiment, said articulated links respectively comprise one or more bearings for rolling.

In an embodiment, the travel of said support is more than 400 mm, more particularly more than 500 mm. This allows for a large travel range corresponding to a large range of object image distances useful for the medical imaging system.

In an embodiment, said C-arm is the C-arm of an X-ray medical imaging system and said support is a support adapted to receive an X-ray detector. In this embodiment, the compromise between flexibility and image quality is especially tough to reach.

In an embodiment, the invention also provides a medical imaging system including a C-arm according to embodiments of the invention and a radiation detector mounted on said support.

In an embodiment, the invention also provides a medical imaging method using medical imaging system according to embodiments of the invention to increase or to decrease the object image distance.

Further features and advantages of the invention will appear from the following description of embodiments of the invention, given as non-limiting examples, with reference to the accompanying drawings listed hereunder.

BRIEF DESCRIPTION OF THE DRAWINGS

FIG. 1 shows a cross section view of an example of a C-arm of a medical imaging system according to an embodiment of the invention.

FIG. 2 shows a view in perspective of an example of a C-arm of a medical imaging system according to an embodiment of the invention.

FIG. 3 shows a view in perspective of an example of a pair of links of the connection between radiation detector support and C-shaped structure of a C-arm of a medical imaging system according to an embodiment of the invention.

FIG. 4 shows a cross section view of an example of a C-shaped structure of a C-arm of a medical imaging system according to an embodiment of the invention.

DETAILED DESCRIPTION OF THE INVENTION

FIG. 1 shows a cross section view of an example of a C-arm of a medical imaging system according to an embodiment of the invention. The C-arm 1 comprises a C-shaped structure 14 which is hollow. Here the casing where the connection 6 is stored is the hollow C-shaped structure 14. The C-shaped structure 14 is ended by an extension comprising, first a hollow bent portion 2 and then a hollow straight portion 3. The outside opening of the hollow straight portion 3 is the end 11 of the C-shaped structure 14 of the C-arm 1.

A support 13 is adapted to receive a radiation detector not shown on FIG. 1 for sake of simplicity. The radiation detector is to be fixed under the support 13. A connection 6 comprises a chain 4 and an actuator 12. The actuator 12 is adapted to push the chain 4 to spread it outside the C-shaped structure 14 and to pull the chain 4 to store it inside the C-shaped structure 14, as is shown by the double arrow 12 symbolizing the actuator 12. The chain 4 comprises several links 5 articulated together. Among those links 5, there are links 5a which are blocked in alignment with one another and with the support 13. This linear rigid alignment of the links 5a with one another and with the support 13 is symbolized by the double arrow 10. Since the last link 5a is still within the hollow straight portion of the C-shaped structure 14, the stability of the support 13 is good and the image quality will be satisfactory. Among those links 5, there are also links 5b which are free with one another and which constitute a bent part of the chain 4. Only five links 5 are shown on FIG. 1 for sake of simplicity, but in reality there may be for example seven or eight links 5.

When the support 13 is going downwards to reduce the object image distance, more and more free links 5b become locked links 5a, that is to say rigidly linearly aligned with one another and with support 13 as well. Actuator 12 is pushing the chain 4 outside C-shaped structure 14 to spread it. Remaining free links 5b constitute the bent part of the chain 4 whereas locked links 5a constitute the straight part of the chain 4. When the support 13 is going upwards to increase the object image distance, more and more locked links 5a become free links 5b, that is to say no more rigidly linearly aligned with one another and with support 13. Actuator 12 is pulling the chain 4 inside C-shaped structure 14 to store it. Free links 5b constitute the bent part of the chain 4 whereas remaining locked links 5a constitute the straight part of the chain 4.

The links 5 are rotary articulated together. The links 5 each present a convex shape at the front which is the front when the links 5 are moving from inside towards outside of C-shaped structure 14, and present a flat shape at the rear which is the rear when the links 5 are moving from inside towards outside of C-shaped structure 14.

The length L2 of the extension of the C-shaped structure 14 is about one and half longer than the length L1 of a single link 5. That way, one link 5 which is going to exit this extension is always aligned and locked with another link 5 inside the extension, before leaving itself the extension. Therefore, all links 5 outside the C-shaped structure 14 are locked together in a rigidly linear alignment.

The length L1 of each link 5 is higher than its thickness T1, more particularly by at least more than 25%. This allows for a fluid sliding of the links within the C-shaped structure 14, without notable risk of gripping because of a tilt of a link 5 within the hollow C-shaped structure 14.

FIG. 2 shows a view in perspective of an example of a C-arm of a medical imaging system according to an embodiment of the invention. It can be seen that each link 5 of the chain 4 has one bearing 7 on each of its sides. These bearings 7 have a function of making easier the sliding of the chain 4 inside the hollow C-shaped structure 14. A cross section of the hollow C-shaped structure 14 is shown and will be detailed in FIG. 4. A is the area of the hollow cross section of the C-shaped structure 14.

The links 5 are rotary articulated together. The links 5 each present a convex shape at the front which is the front when the links 5 are moving from outside towards inside of C-shaped structure 14, and present a flat shape at the rear which is the rear when the links 5 are moving from outside towards inside of C-shaped structure 14. In an embodiment, this orientation is preferred compared to the orientation of FIG. 1, because the convex shape first is more useful when entering the hollow C-shaped structure 14 than when leaving the hollow C-shaped structure 14, in order not to abut against the end 11 of the C-shaped structure 14.

FIG. 3 shows a view in perspective of an example of a pair of links of the connection between radiation detector support and C-shaped structure of a C-arm of a medical imaging system according to an embodiment of the invention. Two links 5 are shown with two locking devices 8 in between. Those locking devices 8 can either block the rotation between the two links 5 or let this rotation free. Each blocking device 8 can comprise two disks which, when separated from each other, let the rotation free between the two links 5, and, when in close contact to each other, block the relative rotation of the two links 5. These locking devices 8 may be actuated in several different ways. One way to actuate the locking devices 8 is a rack and pinion system. Another way to actuate the locking devices 8 is a stator and rotor system. Still another way to actuate the locking devices 8 is an electric jack.

FIG. 4 shows a cross section view of an example of a C-shaped structure of a C-arm of a medical imaging system according to an embodiment of the invention. A is the area of the hollow cross section of the C-shaped structure 14. A is more than half the area of the total cross section of the C-shaped structure 14. Guiding rails 9 are visible. The bearings 7, which have been described in FIG. 2, will roll on these guiding rails 9.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A C-arm of a medical imaging system, comprising:
a C-shaped structure;
a radiation detector support; and
a connection linking said support to said C-shaped structure so that said support is movable toward and away from an end of said C-shaped structure, wherein at least a part of said connection bends when positioned in a hollow section of the C-shaped structure.

2. The C-arm according to claim 1, wherein said connection is at least partly storable in said hollow section of said C-shaped structure when said support is closest to said end of said C-shaped structure.

3. The C-arm according to claim 2, wherein an area of said hollow section of said C-shaped structure is at least more than a half an area of a total section of said C-shaped structure.

4. The C-arm according to claim 2, wherein said C-shaped structure successively comprises, from said end of said C-shaped structure, a hollow straight portion and a hollow bent portion, through which both portions said connection can move forward and backward.

5. The C-arm according to claim 2, wherein said hollow straight portion presents a length which ranges from 1.1 to 1.5 the length of an articulated link.

6. The C-arm according to claim 1, wherein the travel of said support is more than 400 mm.

7. The C-arm according to claim 1, wherein said C-arm is a C-arm of an X-ray medical imaging system and said support is configured to receive an X-ray detector.

8. A medical imaging system comprising the C-arm according to claim 1.

9. A C-arm of a medical imaging system, comprising:
a C-shaped structure;
a radiation detector support; and
a connection linking said support to said C-shaped structure so that said support is movable toward and away from an end of said C-shaped structure, said connection being partly stored in a casing when said support is farthest from said end of said C-shaped structure, wherein the whole part of said connection which is outside said casing is rigidly straight and at least part of said connection which is inside said casing is bent.

10. The C-arm according to claim 9, wherein the whole part of said connection which comes out of said casing is automatically locked in straight position before it comes out of said casing and wherein part of said connection which comes into said casing is automatically made bendable after it comes into said casing.

11. A C-arm of a medical imaging system, comprising:
a C-shaped structure;
a radiation detector support; and
a connection linking said support to said C-shaped structure so that said support is movable toward and away from an end of said C-shaped structure, wherein said connection is configured to be bendable and comprises a chain comprising a plurality of links rotary articulated together.

12. The C-arm according to claim 11, wherein said connection comprises an actuator adapted to push said chain to spread it and to pull said chain to store it.

13. The C-arm according to claim 11, wherein said chain comprises between 4 and 12 articulated links.

14. The C-arm according to claim 11, wherein, said articulated links having a length in direction of their displacement and a thickness in direction of a curvature of said C-shaped structure, said length is bigger than said thickness, said length ranges from 1.1 to 2 times said thickness.

15. The C-arm according to claim 11, wherein; said articulated links having a length in direction of their displacement, said length ranges from 80 mm to 150 mm.

16. The C-arm according to claim 11, wherein said articulated links present a convex shape at the front and the front of said articulated links is stored before rear of said articulated links.

17. The C-arm according to claim 11, wherein said articulated links respectively comprise one or more bearings for rolling.

18. The C-arm according to claim 11, wherein said articulated links present a convex shape at the front and present a flat shape at the rear and the front of said articulated links is stored before rear of said articulated links.

* * * * *